(12) United States Patent
Flachsmann et al.

(10) Patent No.: US 7,638,118 B2
(45) Date of Patent: Dec. 29, 2009

(54) AMINOALKYL SUBSTITUTED ESTERS AND AMIDES OF FUMARIC ACID FOR NEUTRALIZING MALODOR

(75) Inventors: Felix Flachsmann, Duebendorf (CH); Markus Gautschi, Zeiningen (CH)

(73) Assignee: Givaudan SA, Vernier (CH)

( * ) Notice: Subject to any disclaimer, the term of this patent is extended or adjusted under 35 U.S.C. 154(b) by 440 days.

(21) Appl. No.: 10/569,990

(22) PCT Filed: Aug. 20, 2004

(86) PCT No.: PCT/CH2004/000525

§ 371 (c)(1),
(2), (4) Date: Feb. 28, 2006

(87) PCT Pub. No.: WO2005/021051

PCT Pub. Date: Mar. 10, 2005

(65) Prior Publication Data

US 2007/0009475 A1    Jan. 11, 2007

(30) Foreign Application Priority Data

Sep. 2, 2003 (GB) ................... 0320441.9

(51) Int. Cl.
*A61L 9/00* (2006.01)
*C07C 69/34* (2006.01)
(52) U.S. Cl. ............... 424/76.2; 544/111; 560/190; 560/191; 560/196; 562/568
(58) Field of Classification Search ............... 424/76.2; 560/190, 191, 196; 562/568; 544/111
See application file for complete search history.

(56) References Cited

U.S. PATENT DOCUMENTS

| | | |
|---|---|---|
| 3,077,457 A | 2/1963 | Kulka |
| 3,580,918 A | 5/1971 | Bodnarjuk et al. |
| 5,601,809 A | 2/1997 | Davis |
| 5,723,558 A * | 3/1998 | Oishi et al. .............. 526/277 |
| 2003/0135172 A1* | 7/2003 | Whitmore et al. ........... 604/359 |

FOREIGN PATENT DOCUMENTS

| | | |
|---|---|---|
| EP | 0790252 A | 8/1997 |
| FR | 1588375 | 4/1970 |
| GB | 969347 | 9/1964 |
| GB | 1 206 359 | 9/1970 |
| GB | 1 401 550 | 7/1975 |
| GB | 2 002 227 A | 2/1979 |
| JP | 61-283694 * | 7/1993 |
| WO | WO 02/051788 | 7/2002 |

OTHER PUBLICATIONS

McCarthy et al, Journal of Pharmaceutical Sciences, vol. 52, No. 12, 1963, pp. 1168-1171.*
The International Search Report dated Jan. 21, 2005 for application PCT/CH2004/000525.
The Written Opinion of the International Searching Authority for application PCT/CH2004/000525.
The Search Report from The Patent Office in Great Britain dated Jan. 21, 2005 for application GB 0320441.9.
Journal of Pharmacology and Experimental Therapeutics vol. 116, 1956, Frederick C. Uhle et al., "Synthetic esters of dimethylaminoethanol exhibiting positive inotropic cardiac activity", pp. 444-449.
Xiao-Nong Zeng et al., Journal of Chemical Ecology, vol. 17, No. 7, 1991, p. 1469-1492.
B.G. Green et al., Chemical Senses, vol. 21, pp. 323-334, 1996.

* cited by examiner

*Primary Examiner*—Shailendra Kumar
(74) *Attorney, Agent, or Firm*—Norris, McLaughlin & Marcus, PA

(57) ABSTRACT

The present invention relates to aminoalkyl substituted fumarates and there use as malodor neutralizers.

15 Claims, 1 Drawing Sheet

AMINOALKYL SUBSTITUTED ESTERS AND AMIDES OF FUMARIC ACID FOR NEUTRALIZING MALODOR

The present invention refers to malodor neutralising compounds and to compositions containing them. More particularly, the present invention refers to the use of certain aminoalkyl substituted fumarates as malodor neutralisers.

Malodors are offensive odors, which are encountered in the air and on many substrates such as fabrics, hard surfaces, skin, and hair. Malodors have either personal or environmental origin. For example sweat, urine, and feces malodors are personal in origin, whereas kitchen and cooking malodors are of environmental origin. While personal malodors are easily deposited on fabric, hair, and skin, environmental malodors also have a propensity to deposit on these substrates.

Amines, thiols, sulfides, short chain aliphatic and olefinic acids, e.g. fatty acids, are typical of the chemicals found in and contributed to sweat, household, and environmental malodors. These types of malodors typically include indole, skatole, and methanethiol found in toilet and animal odors; piperidine and morpholine found in urine; pyridine and triethyl amine found in kitchen and garbage odors; and short chain fatty acids, such as 3-methyl-3-hydroxyhexanoic acid, 3-methylhexanoic acid or 3-methyl-2-hexenoic acid, found in axilla malodors. Compounds which have been found in the axilla are described for example by Xiao-Nong Zeng et al., Journal of Chemical Ecology, Vol. 17, No. 7, 1991 page 1469-1492, which is incorporated herein by reference.

The capability of fumaric acid esters to bind malodorous substances by chemical reaction has been known for a long time. For example, U.S. Pat. No. 3,077,457 describes the deodorization of a space by spraying into the space a composition comprising a di-ester of fumaric acid, such as di-butyl fumarate, di-hexyl fumarate, di-geranyl fumarate or di-benzyl fumarate. These compositions have been found to reduce tobacco smoke odor and kitchen odor. The use of $C_{1-3}$ dialkylfumarate and $C_{2-3}$ dialkenylfumarate for deodorising air is described in GB 1401550. So called "sulthydryl reactant", i.e. a compound which chemically reacts with a sulfhydryl group, is disclosed in U.S. Pat. No. 5,601,809. This "sulfhydryl reactant" is exemplified by compounds such as diethyl fumarate, di-n-butyl maleate and N-ethylmaleimide. It is said that these compounds are effective against axillary malodor in general, without giving any details concerning the individual compound being responsible for the malodor. However it is well known that not only thiols, i.e. compounds comprising a sulfhydryl group, are responsible for the axillary malodor, but also a large number of acids as described for example by Xiao-Nong Zeng et al. The use of certain aromatic unsaturated carboxylic acid esters in combination with alkyl fumarates as malodor counteractants is disclosed in WO02/051788. Although the compounds known in the art have the ability to neutralise certain malodors, there still remains a need for further compounds which are even more efficient against malodors.

Surprisingly, the inventors now found a new class of compounds capable of neutralising malodors. The literature has not previously described the use as malodor neutraliser of aminoalkyl substituted fumarates, i.e. a compound comprising the skeleton of the fumaric acid wherein either at least one hydrogen of the hydroxy groups is substituted with a hydrocarbon group comprising a secondary or tertiary nitrogen atom or at least one hydroxygroup is replaced by an alkylamine group or dialkylamine group.

Accordingly, the present invention refers in a first aspect to the use as malodor neutralisers of aminoalkyl substituted fumarates.

More particular the present invention refers to the use as malodor neutraliser of an aminoalkyl substituted fumarate of the formula (I)

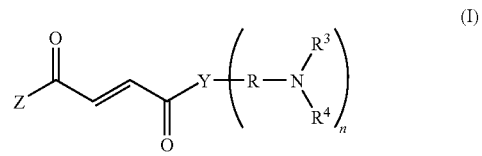

wherein
Z is —$OR^2$ or —Y—(R—$NR^5R^6$)$_n$;
R is linear or branched $C_2$-$C_9$ alkyl, e.g. pentyl, 1,2-dimethyl propyl and methylethyl, preferably $C_2$-$C_4$ alkyl, e.g. ethyl and propyl; linear or branched $C_3$-$C_{18}$ alkoxyalkyl, e.g. ethoxyethyl, and methoxyethyl; phenyl; linear or branched $C_7$-$C_{15}$ phenoxyalkyl, e.g. phenoxyethyl; or linear or branched $C_8$-$C_{16}$ benzoyloxyalkyl;
$R^2$ is linear or branched $C_1$-$C_8$ alkyl, $C_3$-$C_{12}$ cycloalkyl or $C_4$-$C_{13}$ alkylcycloalkyl wherein the cycloalkyl ring is optionally substituted with $C_1$-$C_6$ alkyl; or
$R^2$ is linear or branched $C_1$-$C_8$ alkyl containing at least one oxygen atom, $C_3$-$C_{12}$ cycloalkyl containing at least one oxygen atom and wherein the cycloalkyl ring is optionally substituted with $C_1$-$C_6$ alkyl, or $C_4$-$C_{13}$ alkylcycloalkyl containing at least one oxygen atom and wherein the cycloalkyl ring is optionally substituted with $C_1$-$C_6$ alkyl;
$R^3$ and $R^5$ are independently hydrogen; phenyl; linear or branched $C_1$-$C_{10}$ alkyl, preferably $C_1$ to $C_3$ alkyl, e.g. ethyl, methyl, isopropyl; or linear or branched $C_1$-$C_{10}$ alkyl containing at least one oxygen atom;
$R^4$ and $R^6$ are independently linear or branched $C_1$-$C_{10}$ alkyl, preferably $C_1$ to $C_6$ alkyl, e.g. methyl and ethyl; or linear or branched $C_1$-$C_{10}$ alkyl containing at least one oxygen atom; or
$R^3$ and $R^4$, or $R^5$ and $R^6$ are forming together with the nitrogen atom to which they are attached an aliphatic or aromatic heterocyclic ring system having 3 to 6 ring atoms, e.g. piperidyl; the ring system can optionally contain one oxygen atom or an additional nitrogen atom, e.g. piperazyl, imidazyl, or morpholizyl; and the ring system can optionally bear one or more linear or branched $C_1$-$C_6$ alkyl groups, $C_5$-$C_6$ cycloalkyl groups, or $C_5$-$C_6$ aryl groups; and
(a) when n is 1, Y is oxygen or $NR^1$ wherein
$R^1$ is hydrogen, linear of branched $C_1$-$C_8$ alkyl, $C_3$-$C_{12}$ cycloalkyl or alkylcycloalkyl; or
$R^1$ is linear of branched $C_1$-$C_8$ alkyl substituted with oxygen atoms, $C_3$-$C_{12}$ cycloalkyl substituted with oxygen atoms, or alkylcycloalkyl substituted with oxygen atoms;
(b) when n is 2, Y is nitrogen.

Particularly preferred are compounds of formula (I) selected from but-2-enedioic acid 2-(2-dimethylamino-ethoxy)-ethyl ester ethyl ester, but-2-enedioic acid bis-[2-(2-dimethylamino-ethoxy)-ethyl]ester, 3-[bis-(3-dimethylamino-propyl)-carbamoyl]-acrylic acid ethyl ester, but-2-enedioic acid bis-(2-morpholin-4-yl-ethyl)ester, but-2-enedioic acid bis-(3-dimethylamino-propyl)ester and but-2-enedioic acid bis-(2-dimethylamino-ethyl)ester.

In one preferred embodiment the compounds of formula (I) according to the present invention are symmetric, i.e. Z is —Y—(R—$NR^5R^6$)$_n$ and $R^3$=$R^5$ and $R^4$=$R^6$.

Compounds according to the present invention wherein R is a linear or branched alkyl group are preferred.

The inventors found that compounds according to the present invention are capable of neutralising malodor compounds comprising a functional group selected from —SH, $SH_2$, —NHR, —$NH_2$, or —COOH by chemical reaction with said group, thus neutralising the malodor. Furthermore, aminoalkyl substituted fumarates are capable to react with ammonia by chemical reaction. Surprisingly, it was found that the compounds of the present invention are much more active against malodor compounds as for example dihexylfumarate (DHF), as is illustrated in the examples. Thus, a much lower concentration of a compound of the present invention is necessary to achieve a malodour reduction similar to the one obtained from DHF. Dihexylfumarate has already been used for a long time as a malodor counteractant and thus has been chosen as a comparison example. The compounds of the present invention and the compounds resulting from reaction with the malodor are essentially odourless.

By "active" is meant the reduction of a headspace concentration in % of a malodor compound. It is believed that the reduction is due to a chemical reaction of the malodor neutralising compound of the present invention with the malodor compound. The headspace was analyzed by analysing a defined volume of the headspace of a test sample by GC-MS, as is described in more detail in the examples.

The compounds according to the present invention may be incorporated into a broad range of consumer products either by directly admixing the compound to the consumer product or by admixing a composition comprising a compound of formula (I), e.g. an alcoholic or aqueous solution containing further ingredients such as fragrances, which may then be mixed to the consumer product, using conventional techniques and methods.

Thus, the invention additionally provides a method of manufacturing a composition comprising a compound of formula (I) as an active ingredient. It furthermore provides a method of manufacturing a consumer product comprising said compound as an active ingredient.

The amount of a compound of the present invention required for effective malodor neutralization depends upon the type of product into which such a compound is incorporated. It may further depend upon the ambient conditions, such as humidity and pH. For example, if used in a deodorant spray or room deodorizing spray, the product may comprise from about 0.01 to about 10% wt/wt of the final product, preferably from about 0.1 to about 1% wt/wt. If used in a room deodorizing filter device, i.e. a cooker hood, the amount of the compound may range from about 0.1% to about 20% wt/wt of the filter weight.

A further aspect of the present invention is a method for imparting malodor neutralizing effects to a substrate, e.g. skin, hair or fabrics, comprising the step of contacting a substrate with a consumer product comprising a compound of formula (I).

The present invention also includes a process for dispersing a consumer product comprising an aminoalkyl substituted fumarate of the present invention into a confined space, e.g. rooms, closets, chests, and draws. This process includes incorporating into a consumer product a compound of formula (I) and dispersing an effective amount of the consumer product into the space, e.g. by spraying, atomising and/or volatilising.

As used herein, "consumer products" include, for example cosmetic products, deodorants, antiperspirants, and home care and fabric care products, such as air-fresheners, surface cleaners, detergents, fabric conditioners, rinsing conditioners for fabrics and products for application to garments, upholstery, curtains, carpets, absorbent materials, e.g a filter. The product may be in form of a liquid, e.g. for application to a surface by pouring or spraying; a solid, e.g. a powder or compact powder, or in form of a candle; or a semisolid, such as a gel.

The compounds of formula (I) wherein Z is —Y—(R—$NR^3R^4$) and Y is oxygen, i.e. symmetric diesters, may be prepared by reaction of maleic anhydride with an excess of the corresponding alcohol in the presence of $Fe_2(SO_4)_3$ as a catalyst under removal of water, as described for example in FR1588375. Alternatively, fumaric acid dichloride is reacted with 2 equivalents of H—Y—R—$NR^3R^4$ in the presence of a base, such as pyridine or N,N-diethyl ethanamine.

Asymmetrical diester (3) as defined by the present invention may be prepared by reaction of the corresponding fumaric acid monoester (1) with thionyl chloride, phosphorous trichloride, phosphoric trichloride, or oxalic acid dichloride to form the corresponding fumaryl chloride (2), which is then reacted with H—Y—R—$NR^3R^4$ in the presence of a base, for example pyridine or N,N-diethyl ethanamine as shown in Scheme 1. Monoester (1) in turn may be prepared by reaction of maleic anhydride with H—Z and double bond isomerisation under conditions known to the person skilled in the art.

Scheme 1:

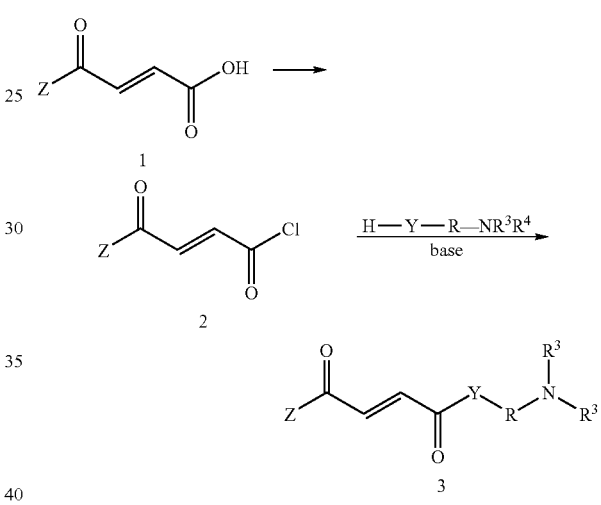

Figure 1:
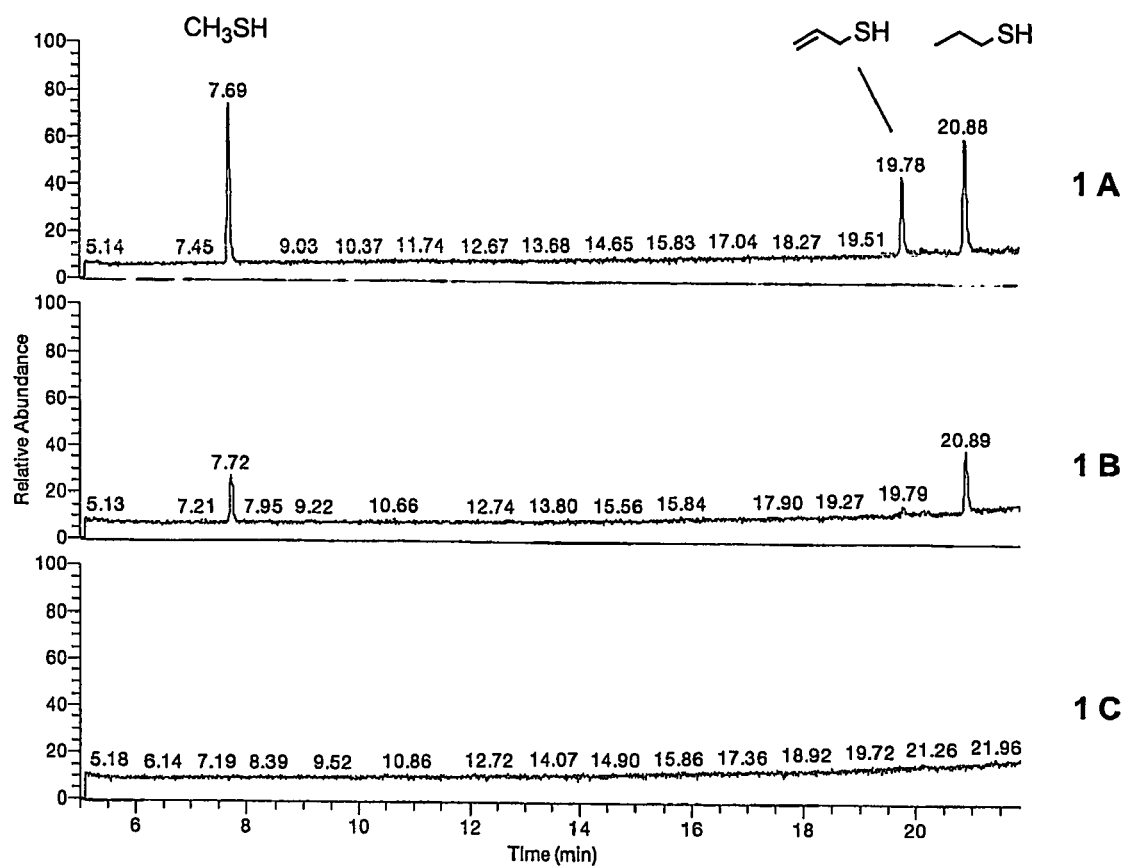
FIG. 1 shows a typical GC-MS chromatogram of the headspace of a blank sample (1A), a sample charged with DHF (1B), and a sample charged with a compound 8 (1C).

The invention is now further described with reference to the following non-limiting examples.

EXAMPLE 1

But-2-enedioic acid
2-(2-dimethylamino-ethoxy)-ethyl ester ethyl ester

To the solution of 2-[2-(dimethylamino)-ethoxy]ethanol (13.35 g, 100 mmol, 1.9 equiv.) and 4-dimethylaminopyridine (50 mg) in toluene (80 ml) is added a solution of fumaric acid monoethylester monochloride (8.50 g, 52 mmol, 1.0 equiv.) in toluene (20 ml) at 23° C. over 25 min. The temperature rises to 34° C. and an orange suspension is formed. After 5 h stirring at room temperature, the mixture is poured on ice-cooled saturated aqueous $NaHCO_3$ solution and the product is extracted with ethyl acetate. The organic layer is washed 3 times with $H_2O$, then twice with brine. It is then dried over $MgSO_4$ and concentrated in a rotary evaporator. The residue is dissolved in methyl t-butyl ether and SiO$_2$ (6.0 g) is added to the solution. The suspension is shaken vigorously, then filtered and again concentrated and dried under high vacuum (23° C., 0.05 mbar). This yields the product (6.71 g, 50%) as a yellow liquid.

IR (film): 1719vs, 1647 w, 1295 vs, 1258 vs, 1155 vs, 1035 s.

$^1$H-NMR (400 MHz, CDCl$_3$): 6.88 (s, 1H), 6.87 (s, 1H), 4.38-4.35 (sym. m, 2H), 4.26 (q, J=7.2, 2H), 3.74-3.71 (sym. m, 2H), 3.60 (t, J=6, 2H), 2.52 (t, J=5.6, 2H), 2.28 (s, 6H), 1.32 (t, J=7.2, 3H).

$^{13}$C-NMR: 164.8 (s), 164.8 (s), 133.9 (d), 133.2 (d), 69.3 (t), 68.6 (t), 64.3 (t), 61.2 (t), 58.7 (t), 45.8 (q), 14.0 (q).

MS (EI 70 eV): 259 (<1, M$^+$), 214 (<1), 116(4), 72 (6), 58 (100).

EXAMPLE 2

But-2-enedioic acid bis-[2-(2-dimethylamino-ethoxy)-ethyl]ester

The solution of 2-[2-(dimethylamino)-ethoxy]ethanol (6.65 g, 50 mmol, 2.5 equiv.) and 4-dimethylaminopyridine (11 mg) in toluene (20 ml) is cooled to −20° C. Separate solutions of fumaryl chloride (2.3 ml, 20 mmol, 1.0 equiv.) and 1,1,3,3-tetramethylguanidine (5.0 ml, 40 mmol, 2.0 equiv.) in toluene (each 25 ml) are added dropwise simultaneously via syringe pump over 80 min. A dark suspension is formed. After complete addition, the cooling bath is removed and stirring continued at 23° C. for 40 min. Active charcoal (1.0 g) is added and the mixture is filtered over a short pad of basic Al$_2$O$_3$, which is further rinsed with toluene/EtOAc (360 ml). The solution is concentrated and dried in vacuo (0.05 mbar) to yield the product as a yellow oil (2.79 g, 40%).

IR (film): 1722vs, 1646w, 1294s, 1258s, 1126vs.

$^1$H-NMR (400 MHz, CDCl$_3$): 6.90 (s, 2H), 4.37-4.35 (sym. m, 4H), 3.73-3.31 (sym. m, 4H), 3.59 (t, J=5.6, 4H), 2.52 (t, J=5.6, 4H), 2.27 (s, 12H).

$^{13}$C-NMR: 164.3 (s), 133.5 (d), 69.3 (t), 68.6 (t), 64.3 (t), 58.7 (t), 45.8 (q).

MS (EI 70 eV): 345 (<1, [M−1]$^+$), 276 (7), 72 (19), 58 (100).

EXAMPLE 3

But-2-enedioic acid bis-(2-morpholin-4-yl-ethyl)ester

Following the general procedure described in Example 2, 4-(2-hydroxyethyl)-morpholin (105 mmol) is reacted with fumaryl chloride (50 mmol) in toluene in the presence of 4-dimethylaminopyridine (cat.) and 1,1,3,3-tetramethylguanidine (100 mmol). The product was obtained as a pure crystalline solid after crystallisation from methyl t-butyl ether (yield: 35%).

IR (film): 1715vs, 1294vs, 1150vs, 1111vs.

$^1$H-NMR (400 MHz, CDCl$_3$): 7.00 (s, 2H), 4.34 (t, J=4, 4H), 3.72-3.69 (sym. m, 8H), 2.68 (t, J=4, 4H), 2.53-2.50 (sym. m, 8H).

$^{13}$C-NMR: 164.8 (s), 133.6 (d), 66.8 (t), 62.4 (t), 56.9 (t), 53.8 (t).

MS (EI 70 eV): 342 (9, M$^+$), 113 (63), 100 (100).

EXAMPLE 4

But-2-enedioic acid bis-(2-dimethylamino-ethyl)ester

Following the general procedure described in Example 2, N,N-dimethylaminoethanol (50 mmol) is reacted with fumaryl chloride (20 mmol) in toluene in the presence of 4-dimethylaminopyridine (cat.) and 1,1,3,3-tetramethylguanidine (40 mmol). The product is obtained as a yellow oil (yield: 72%).

IR (film): 1720vs, 1339s, 1257s, 1155vs.

$^1$H-NMR (400 MHz, CDCl$_3$): 6.90 (s, 2H), 4.30 (t, J=5.6, 4H), 2.62 (t, J=5.6, 4H), 2.29 (s, 12H).

$^{13}$C-NMR: 164.9 (s), 133.6 (d), 63.0 (t), 57.6 (t), 45.7 (q).

MS (EI 70 eV): 258 (<1, M$^+$), 188 (2), 71 (13), 58 (100).

EXAMPLE 5

3-[bis-(3-dimethylamino-propyl)-carbamoyl]-acrylic acid ethyl ester 3,3'-Iminobis(N,N-dimethyl-propylamine) (10.66 g, 55 mmol) and DMAP (54 mg) are dissolved in toluene (60 ml). To this solution is added the solution of fumaric acid mono-ethyl ester mono chloride (8.15 g, 50 mmol) in toluene (20 ml) over 20 min via syringe pump. The mixture is further stirred for 3 h at 23° C., then poured on a mixture of ice and sat. aq. NaHCO$_3$-solution. The product is extracted twice with EtOAc (100 ml) and the organic layers washed twice with brine, combined and dried over MgSO$_4$.

The crude (dark oil, 2.80 g) is suspended in methyl t-butyl ether, SiO$_2$ (3 g) is added and the mixture shaken vigorously, then filtered, concentrated and dried at 0.01 mbar/23° C. The product is obtained as a brown oil (1.95 g, 12%).

IR (film): 2941m, 2766m, 1721vs, 1652s, 1624s, 1267vs.

$^1$H-NMR (400 MHz, CDCl$_3$): 7.52 (d, J=11.4, 1H), 6.81 (d, J=11.4, 1H), 4.25 (q, J=7.2, 2H), 3.45 (q, J=8, 4H), 2.33-2.20 (m, 4H), 2.24 (s, 6H), 2.21 (s, 6H), 1.82-1.70 (m, 4H), 1.32 (t, J=4, 3H).

$^{13}$C-NMR: 165.7(s), 164.5 (s), 134.2 (d), 131.0 (d), 60.9 (t), 56.9 (t), 55.8 (t), 46.0 (t), 45.3 (q), 45.2 (q), 44.7 (t), 27.3 (t), 25.6 (t), 14.1 (q).

MS (EI 70 eV): 313 (7, M$^+$), 298 (14), 269 (77), 226 (80), 176 (100),) 71 (13), 58 (100).

EXAMPLE 6

Quantitative Monitoring of Thiol Neutralizing Activity

A 23×75 mm headspace vial is charged with 0.20 ml of a 5 mM solution of the test substance in MeOH/H$_2$O (9:1), i.e. DHF, but-2-enedioic acid 2-(2-dimethylamino-ethoxy)-ethyl ester ethyl ester (1), but-2-enedioic acid bis-[2-(2-dimethylamino-ethoxy)-ethyl]ester (2), 3-[bis-(3-dimethylamino-propyl)-carbamoyl]-acrylic acid ethyl ester (3), but-2-enedioic acid bis-(2-morpholin-4-yl-ethyl)ester (4), but-2-enedioic acid bis-(2-dimethylamino-propyl)ester (5), and but-2-enedioic acid bis-(2-dimethylamino-ethyl)ester (6) each. In addition a blank sample with 0.20 ml of MeOH/H$_2$O 9:1 is prepared. Then the vials are sealed with a 20 mm-aluminium seal containing a rubber septum and sulfur malodor mixture (0.20 ml) as described below is added to each sample via cannula through the septum.

Sulfur malodor mixture (in MeOH/H$_2$O, 9:1):

| | Conc. [mM] |
|---|---|
| Methyl mercaptane (A) | 0.7 |
| Prop-2-ene-1-thiol (B) | 1.0 |
| 1-Propanthiol (C) | 1.0 |

The samples are left at room temperature for 2 h, then submitted to the headspace analysis using a headspace autosampler connected to a GC-MS apparatus. Per sample, 250 μl of headspace is injected with a 1:200 split ratio onto a Chrompack PoraBOND Q column (ex. Varian Inc.). The peak areas (MS-ion current) of each single compound of the sulfur malodor mixture were compared to the corresponding values from the blank samples to calculate the reduction of headspace concentration. The results are listed in table 1 below. FIG. 1 shows a typical GC-MS chromatogram of the headspace of a blank sample (1A), a sample charged with DHF (1B), and a sample charged with a compound 8 (1C).

TABLE 1

Headspace reduction

| | % Headspace reduction of | | |
|---|---|---|---|
| Compound | Methyl-SH (A) | Propyl-SH (C) | Allyl-SH (B) |
| DHF (comparison example) | 71 | 42 | 100 |
| 1 | 100 | 100 | 100 |
| 2 | 100 | 100 | 100 |
| 3 | 92 | 65 | 100 |
| 4 | 100 | 90 | 100 |
| 5 | 100 | 100 | 100 |
| 6 | 100 | 100 | 100 |

The experiment shows a greatly enhanced neutralizing activity of the dialkylaminofumarates over dihexylfumarate (DHF).

EXAMPLE 7

Quantitative Monitoring of Sweat Acid Neutralizing Activity

Figure 2:
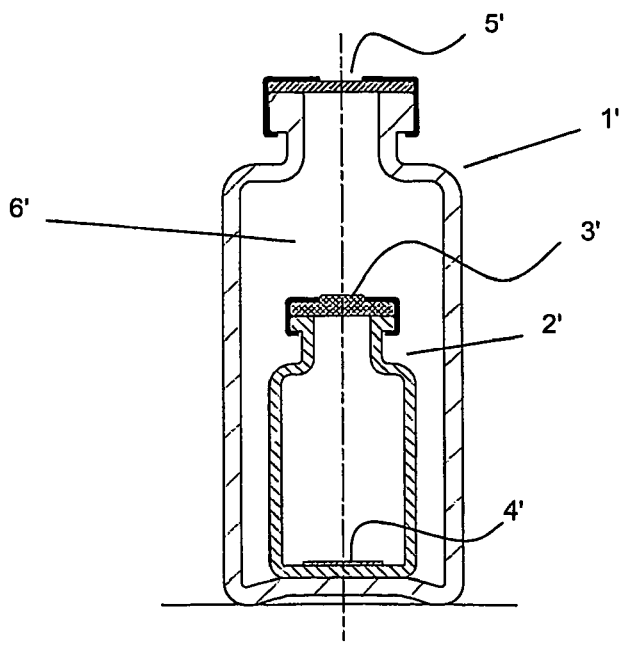
FIG. 2 depicts a two chamber sample.

A two chamber sample was prepared as depicted in FIG. 2. It is composed of the headspace vial (1') described in Example 5 as the outer containment and a standard HPLC-autosampler vial (2') as the inner containment.

The indicated amount of DHF or compound 8 is adsorbed on viscose filter (3') (applied as $CH_2Cl_2$-solution and let evaporate). Then 50 μg of 3-methyl hexanoic acid is adsorbed on paper disk (4') (5 mm Ø, product applied as $CH_2Cl_2$-solution and let evaporate). The screw cap containing filter (3') is screwed tightly on the HPLC-vial (2'), which is placed in the headspace vial (1'). The headspace vial (1') is closed with an aluminium seal containing a rubber septum (5'). The sample is left standing for 16 h at room temperature, then submitted to headspace analysis as described in Example 5.

The acid has to diffuse through the filter (3') coated with DHF or but-2-enedioic acid bis-(2-dimethylamino-ethyl)ester (6) into the outer volume (6'). The results are shown in Table 2 below.

TABLE 2

Reduction of headspace concentration of 3-methyl hexanoic acid by varied amounts of DHF (comparison example) and but-2-enedioic acid bis-(2-dimethylamino-ethyl) ester (6).

| Compound | Amount [mg] | % Headspace reduction |
|---|---|---|
| DHF | 4.5 | 66 |
| DHF | 0.5 | 29 |
| 6 | 4.5 | 100 |
| 6 | 0.5 | 100 |

The experiment shows "complete retention" of the malodorous acid by but-2-enedioic acid bis-(2-dimethylamino-ethyl)ester (6), even at low concentrations, i.e. an amount where dihexylfumarate (DHF) neutralizes only 29% of the malodor (3-methyl hexanoic acid). By "complete retention" is meant that no detectable amount of the acid passes through the filter.

EXAMPLE 7

Olfactory Evaluation Against Sweat-Malodor Reconstitution

An ethanolic solution of axilla-malodor reconstitution is applied on a 1×1 cm cotton swatch (100 μl, 0.1% wt/wt), then 50 μl of the test compound but-2-enedioic acid bis-(2-dimethylamino-propyl)ester (5) and but-2-enedioic acid bis-(2-dimethylamino-ethyl)ester (6) (solution in ethanol at 1% wt/wt) are dosed to the malodor treated swatches. The malodor intensity is rated on a LMS by an expert panel of 20 assessors. The results are then expressed in % reduction relative to malodor of the blank sample. The Labeled Magnitude scale (LMS) is a semantic scale of perceptual intensity characterized by a quasi-logarithmic scaling of its verbal labels, as described by B. G. Green et al., Chemical Senses. Vol. 21, pp 323-334, 1996. The position of the verbal labels on the LMS, as percentage of full scale length, are: barely detectable, 1.4; weak, 6.1; moderate, 17.2; strong, 53.2; strongest imaginable, 100.

TABLE 3

Reduction of axilla malodor intensity in panel test.

| Compound | % Reduction |
|---|---|
| DHF | 68 |
| 5 | 77 |
| 6 | 80 |

The invention claimed is:

1. A method of imparting a malodor neutralizing effects to a substrate comprising contacting the substrate with the aminoalkyl substituted fumarate of formula (I)

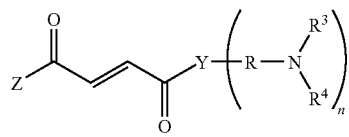

wherein n is 1 or 2;
Z is —$OR^2$ or —Y—(R—$NR^5R^6$)$_n$;
R is linear or branched $C_2$-$C_9$ alkyl, linear or branched $C_3$-$C_{18}$ alkoxyalkyl, phenyl, linear or branched $C_7$-$C_{15}$ phenoxyalkyl, or linear or branched $C_8$-$C_{16}$ benzoyloxyalkyl;
$R^2$ is linear or branched $C_1$-$C_8$ alkyl, $C_3$-$C_{12}$ cycloalkyl or $C_4$-$C_{13}$ alkylcycloalkyl wherein the cycloalkyl ring is optionally substituted with $C_1$-$C_6$ alkyl; or
$R^2$ is linear or branched $C_1$-$C_8$ alkyl containing at least one oxygen atom, $C_3$-$C_{12}$ cycloalkyl containing at least one oxygen atom and wherein the cycloalkyl ring is optionally substituted with $C_1$-$C_6$ alkyl, or $C_4$-$C_{13}$ alkylcycloalkyl containing at least one oxygen atom and wherein the cycloalkyl ring is optionally substituted with $C_1$-$C_6$ alkyl;
$R^3$ and $R^5$ are independently hydrogen, phenyl, linear or branched $C_1$-$C_{10}$ alkyl, or linear or branched $C_1$-$C_{10}$ alkyl containing at least one oxygen atom;
$R^4$ and $R^6$ are independently linear or branched $C_1$-$C_{10}$ alkyl, or linear or branched $C_1$-$C_{10}$ alkyl containing at least one oxygen atom; or
$R^3$ and $R^4$, or $R^5$ and $R^6$ are forming together with the nitrogen atom to which they are attached an aliphatic or aromatic heterocyclic ring system having 3 to 6 ring atoms;
the ring system can optionally contain one oxygen atom or an additional nitrogen atom; and the ring system can optionally bear one or more linear or branched $C_1$-$C_6$ alkyl groups, $C_5$-$C_6$ cycloalkyl groups, or $C_5$-$C_6$ aryl groups; and
a) when n is 1; Y is oxygen or $NR^1$ wherein $R^1$ is hydrogen, linear of branched $C_1$-$C_8$ alkyl, $C_3$-$C_{12}$ cycloalkyl or alkylcycloalkyl; or $R^1$ is linear of branched $C_1$-$C_8$ alkyl substituted with oxygen atoms, $C_3$-$C_{12}$ cycloalkyl substituted with oxygen atoms, or alkylcycloalkyl substituted with oxygen atoms; and
b) when n is 2, Y is nitrogen.

2. A method according to claim 1 wherein the aminoalkyl substituted fumarate is of formula (I), wherein Z is —Y—(R—$NR^5R^6$)$_n$ and $R^3$=$R^5$ and $R^4$=$R^6$.

3. A method according to claim 2 wherein the aminoalkyl substituted fumarate is selected from the group consisting of: but-2-enedioic acid bis-[2-(2-dimethylamino-ethoxy)-ethyl]ester, 3-[bis-(3-dimethylamino-propyl)-carbamoyl]-acrylic acid ethyl ester, and but-2-enedioic acid bis-(2-morpholin-4-yl-ethyl)ester.

4. A method according to claim 1 wherein the aminoalkyl substituted fumarate is but-2-enedioic acid 2-(2-dimethylamino-ethoxy)-ethyl ester ethyl ester.

5. A compound selected from the group consisting of: but-2-enedioic acid 2-(2-dimethylamino-ethoxy)-ethyl ester ethyl ester, but-2-enedioic acid bis-[2-(2-dimethylamino-ethoxy)-ethyl]ester, 3-[bis-(3-dimethylamino-propyl)-carbamoyl]-acrylic acid ethyl ester, and but-2-enedioic acid bis-(2-morpholin-4-yl-ethyl)ester.

6. A consumer product selected from the group consisting of: cosmetic products, home care products and fabric care products comprising as malodor neutraliser an aminoalkyl substituted fumarate.

7. A method of imparting a malodor neutralising effect to a substrate comprising the step of: contacting the substrate with a consumer product according to claim 6.

8. A process for dispersing a consumer product into a space comprising:
(a) incorporating into a consumer product an aminoalkyl substituted fumarate; and
(b) dispersing an effective amount of the consumer product into the space,
wherein the consumer product is selected from home care products.

9. A method according to claim 1 wherein R is a linear or branched $C_2$-$C_9$ alkyl.

10. A consumer product according to claim 6 wherein the cosmetic product is a deodorant or an antiperspirant.

11. A consumer product selected from the group consisting of: cosmetic products, home care products and fabric care products comprising as malodor neutraliser 0.01-20% wt/wt of aminoalkyl substituted fumarate.

12. A consumer product according to claim 6 comprising as malodor neutraliser an aminoalkyl substituted fumarate of the formula (I)

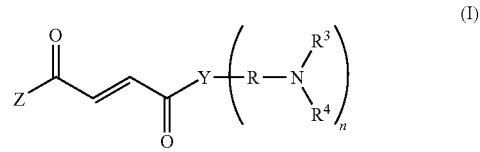

wherein n is 1 or 2;
Z is —$OR^2$ or —Y—(R—$NR^5R^6$)$_n$;
R is linear or branched $C_2$-$C_9$ alkyl, linear or branched $C_3$-$C_{18}$ alkoxyalkyl, phenyl, linear or branched $C_7$-$C_{15}$ phenoxyalkyl, or linear or branched $C_8$-$C_{16}$ benzoyloxyalkyl;
$R^2$ is linear or branched $C_1$-$C_8$ alkyl, $C_3$-$C_{12}$ cycloalkyl or $C_4$-$C_{13}$ alkylcycloalkyl wherein the cycloalkyl ring is optionally substituted with $C_1$-$C_6$ alkyl; or
$R^2$ is linear or branched $C_1$-$C_8$ alkyl containing at least one oxygen atom, $C_3$-$C_{12}$ cycloalkyl containing at least one oxygen atom and wherein the cycloalkyl ring is optionally substituted with $C_1$-$C_6$ alkyl, or $C_4$-$C_{13}$ alkylcycloalkyl containing at least one oxygen atom and wherein the cycloalkyl ring is optionally substituted with $C_1$-$C_6$ alkyl;
$R^3$ and $R^5$ are independently hydrogen, phenyl, linear or branched $C_1$-$C_{10}$ alkyl, or linear or branched $C_1$-$C_{10}$ alkyl containing at least one oxygen atom;
$R^4$ and $R^6$ are independently linear or branched $C_1$-$C_{10}$ alkyl, or linear or branched $C_1$-$C_{10}$ alkyl containing at least one oxygen atom; or
$R^3$ and $R^4$, or $R^5$ and $R^6$ are forming together with the nitrogen atom to which they are attached an aliphatic or aromatic heterocyclic ring system having 3 to 6 ring atoms; the ring system can optionally contain one oxygen atom or an additional nitrogen atom; and the ring system can optionally bear one or more linear or branched $C_1$-$C_6$ alkyl groups, $C_5$-$C_6$ cycloalkyl groups, or $C_5$-$C_6$ aryl groups; and a) when n is 1; Y is oxygen or $NR^1$ wherein $R^1$ is hydrogen, linear of branched $C_1$-$C_8$ alkyl, $C_3$-$C_{12}$ cycloalkyl or alkylcycloalkyl; or $R^1$ is linear of branched $C_1$-$C_8$ alkyl substituted with oxygen atoms, $C_3$-$C_{12}$ cycloalkyl substituted with oxygen atoms, Or alkylcycloalkyl substituted with oxygen atoms; and b) when n is 2, Y is nitrogen.

13. A consumer product selected from the group consisting of: cosmetic products, home care products and fabric care products, comprising as malodor neutraliser an aminoalkyl substituted fumarate of formula (I) according to claim 1 wherein Z is —Y—(R—$NR^5R^6$)$_n$ and $R^3$=$R^5$ and $R^4$=$R^6$.

14. A consumer product selected from the group consisting of: cosmetic products, home care products and fabric care products, comprising as malodor neutraliser an aminoalkyl substituted fumarate of formula (I) according to claim 1 wherein R is a linear or branched $C_2$-$C_9$ alkyl.

15. A consumer product selected from the group consisting of: cosmetic products, home care products and fabric care products, comprising as malodor neutraliser an aminoalkyl substituted fumarate selected from the group consisting of: but-2-enedioic acid 2-(2-dimethylamino-ethoxy)-ethyl ester ethyl ester, but-2-enedioic acid bis-[2-(2-dimethylamino-ethoxy)-ethyl]ester, 3-[bis-(3-dimethylamino-propyl)-carbamoyl]-acrylic acid ethyl ester, and but-2-enedioic acid bis-(2-morpholin-4-yl-ethyl)ester.

* * * * *